United States Patent
Rim et al.

(10) Patent No.: US 9,194,816 B2
(45) Date of Patent: Nov. 24, 2015

(54) METHOD OF DETECTING A DEFECT OF A SUBSTRATE AND APPARATUS FOR PERFORMING THE SAME

(71) Applicant: Samsung Electronics Co., Ltd., Suwon-si (KR)

(72) Inventors: Min-Ho Rim, Hwaseong-si (KR); Yu-Sin Yang, Seoul (KR); Sang-Kil Lee, Yongin-si (KR); Yong-Deok Jeong, Hwaseong-si (KR); Hyung-Suk Cho, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 14/316,173

(22) Filed: Jun. 26, 2014

(65) Prior Publication Data
US 2015/0070690 A1    Mar. 12, 2015

(30) Foreign Application Priority Data
Sep. 6, 2013    (KR) .......................... 10-2013-0106919

(51) Int. Cl.
  *G01N 21/00*   (2006.01)
  *G01N 21/956*   (2006.01)
  *G01N 21/95*   (2006.01)
  *G01N 21/88*   (2006.01)

(52) U.S. Cl.
  CPC .......... *G01N 21/956* (2013.01); *G01N 21/9501* (2013.01); *G01N 2021/8835* (2013.01)

(58) Field of Classification Search
  CPC combination set(s) only.
  See application file for complete search history.

(56) References Cited

U.S. PATENT DOCUMENTS

| | | | |
|---|---|---|---|
| 5,828,457 A | 10/1998 | Tabata et al. | |
| 7,433,033 B2 | 10/2008 | Bleeker et al. | |
| 7,535,563 B1 | 5/2009 | Chen et al. | |
| 7,659,973 B2 | 2/2010 | Furman et al. | |
| 8,004,655 B2 | 8/2011 | Shiratsuchi et al. | |
| 8,031,931 B2 | 10/2011 | Fuchs et al. | |
| 8,206,706 B2 | 6/2012 | Clemmons et al. | |
| 2006/0001890 A1 | 1/2006 | Poultney | |
| 2006/0012781 A1 | 1/2006 | Fradkin et al. | |
| 2012/0229618 A1* | 9/2012 | Urano et al. | 348/92 |
| 2013/0182263 A1* | 7/2013 | Shchegrov et al. | 356/512 |

FOREIGN PATENT DOCUMENTS

| | | | | |
|---|---|---|---|---|
| JP | 10-030988 A | | 2/1998 | |
| JP | 10-068698 A | | 3/1998 | |
| JP | 10221267 A | * | 8/1998 | ............ G01N 21/88 |
| JP | 3185878 B | | 5/2001 | |
| JP | 3573587 B | | 7/2004 | |
| JP | 4010649 B | | 9/2007 | |
| JP | 2011-112449 A | | 6/2011 | |
| JP | 4824451 B | | 9/2011 | |

* cited by examiner

*Primary Examiner* — Tri T Ton
(74) *Attorney, Agent, or Firm* — Myers Bigel Sibley & Sajovec, PA

(57) ABSTRACT

In a method of detecting a defect of a substrate, a first light having a first intensity may be irradiated to a first region of the substrate through a first aperture. A defect in the first region may be detected using a first reflected light from the first region. A second light having a second intensity may be irradiated to a second region of the substrate through a second aperture. A defect in the second region may be detected using a second reflected light from the second region. Thus, the defects by the regions of the substrate may be accurately detected.

7 Claims, 6 Drawing Sheets

METHOD OF DETECTING A DEFECT OF A SUBSTRATE AND APPARATUS FOR PERFORMING THE SAME

CROSS-RELATED APPLICATION

This application claims priority under 35 USC §119 to Korean Patent Application No. 10-2013-0106919, filed on Sep. 6, 2013 in the Korean Intellectual Property Office (KIPO), the contents of which are incorporated by reference herein in their entirety.

FIELD

Example embodiments relate to a method of detecting a defect of a substrate and an apparatus for performing the same. More particularly, example embodiments relate to a method of detecting a defect of a semiconductor substrate, and an apparatus for performing the method.

BACKGROUND

Generally, a defect in a semiconductor substrate may be detected using a light. The light may be irradiated to the semiconductor substrate through an aperture. A light reflected from the semiconductor substrate may be analyzed to detect the defect of the semiconductor substrate.

According to related arts, the defect may be detected using only one aperture. However, recipes for detecting defects for different regions on the semiconductor substrate may be different from each other. Therefore, in order to detect the defects in each of the regions of the semiconductor substrate, the semiconductor substrate may be scanned using the light passing through a first aperture. The semiconductor substrate may then be scanned using the light passing through a second aperture. As a result, the defects may not be accurately detected. Further, a time for detecting the defects may be long.

SUMMARY

Example embodiments provide a method of detecting a defect of a substrate in a short time with improved defect detection.

Example embodiments also provide an apparatus for performing the above-mentioned method.

According to example embodiments, there may be provided a method of detecting a defect of a substrate. In the method of detecting the defect of the substrate, a first light having a first intensity may be irradiated to a first region of the substrate through a first aperture. A defect in the first region may be detected using a first reflected light from the first region. A second light having a second intensity may be irradiated to a second region of the substrate through a second aperture. A defect in the second region may be detected using a second reflected light from the second region.

In example embodiments, the method may further include changing the first light into the second light at a time when an inspection or irradiation region is changed from the first region to the second region.

In example embodiments, the method may further include changing the first aperture into the second aperture at the time when an inspection region is changed from the first region to the second region.

In example embodiments, changing the first aperture into the second aperture may include controlling a spatial light modulator. The first and second apertures may be defined in the spatial light modulator.

In example embodiments, the method may further include changing the first aperture into the second aperture at the time when an irradiation region is changed from the first region to the second region.

In example embodiments, the method may further include setting the first light and the first aperture prior to irradiating the first light to the first region, and setting the second light and the second aperture prior to irradiating the second light to the second region.

In example embodiments, the method may further include setting a first defect detection recipe prior to detecting the defect in the first region, and setting a second defect detection recipe prior to detecting the defect in the second region.

In example embodiments, the method may further include irradiating a third light having a third intensity to a third region of the substrate through a third aperture, and detecting a defect in the third region based on a third reflected light from the third region.

In example embodiments, the method may further include changing the second light into the third light at a time when an inspection region is changed from the second region to the third region, and changing the second aperture into the third aperture at the time when the inspection region is changed from the second region to the third region.

According to example embodiments, there may be provided an apparatus for detecting a defect of a substrate. The apparatus may include an irradiator, a spatial light modulator and a controller. The irradiator may be configured to irradiate a light to the substrate. The spatial light modulator may be arranged between the substrate and the irradiating unit. The spatial light modulator may have an aperture through which the light may pass. The controller may be configured to control the irradiator to provide the light with different intensities for different regions of the substrate. The controller may be configured to control the irradiator to change a size of the aperture for different regions of the substrate. The controller may be configured to detect the defect of the substrate based on a reflected light from the substrate.

In example embodiments, the controller may change intensities of the light at a time when an inspection region is changed from any one region of the substrate to another region of the substrate.

In example embodiments, the controller may be configured to change the size of the aperture at the time when an inspection region is changed from any one region of the substrate to another region of the substrate.

In example embodiments, the controller may change the size of the aperture at a time when the regions of the substrate irradiated by the light may be changed.

In example embodiments, the controller may be configured to store the intensity of the light and the size of the aperture for each of the regions of the substrate.

In example embodiments, the controller may be configured to store defect a detection recipe for each of the regions of the substrate.

According to example embodiments, the spatial light modulator may be controlled in real time in accordance with the regions of the substrate to change the size of the aperture and the intensity of the light so that the defects by the regions of the substrate may be accurately detected. Further, the defect may be detected by only one scanning the substrate so that a time for detecting the defect may be remarkably reduced.

According to other example embodiments, there may be provided a method of detecting a defect of a substrate. The method includes: (a) irradiating a first light having a first intensity to a first region of the substrate through a first aperture defined in a spatial light modulator; (b) determining whether a defect in the first region exists based on a first reflected light from the first region; (c) changing the first aperture into a second aperture defined in the spatial light modulator at a time when an inspection region is changed from the first region to a second region of the substrate; (d) irradiating a second light having a second intensity to the second region of the substrate through the second aperture; and (e) determining whether a defect in the second region exists based on a second reflected light from the second region. In example embodiments, steps (a) to (e) are carried out continuously.

In example embodiments, the method may further include changing the first light into the second light at the time when the inspection region is changed from the first region to the second region.

In example embodiments, the first intensity of the first light and a size of the first aperture may be based on a first inspection recipe of the first region. In example embodiments, the second intensity of the second light and a size of the second aperture are based on a second inspection recipe of the second region.

In example embodiments, the method may further include using a first defect detection recipe to determine whether a defect in the first region exists, and using a second defect detection recipe to determine whether a defect in the second region exists.

BRIEF DESCRIPTION OF THE DRAWINGS

Example embodiments will be more clearly understood from the following detailed description taken in conjunction with the accompanying drawings.

FIGS. 1 to 9 represent non-limiting, example embodiments as described herein.

FIG. 1 is a cross-sectional view illustrating an apparatus for detecting a defect of a substrate in accordance with example embodiments;

FIG. 2 is a plan view illustrating regions of the substrate;

FIG. 3 is a plan view illustrating a spatial light modulator of the apparatus in FIG. 1;

FIG. 4 is a cross-sectional view illustrating operations of the apparatus in FIG. 1;

FIGS. 5 to 8 are digital images showing different apertures of the spatial light modulator by the regions of the substrate in FIG. 3.

DETAILED DESCRIPTION OF THE EMBODIMENTS

Figure 1:
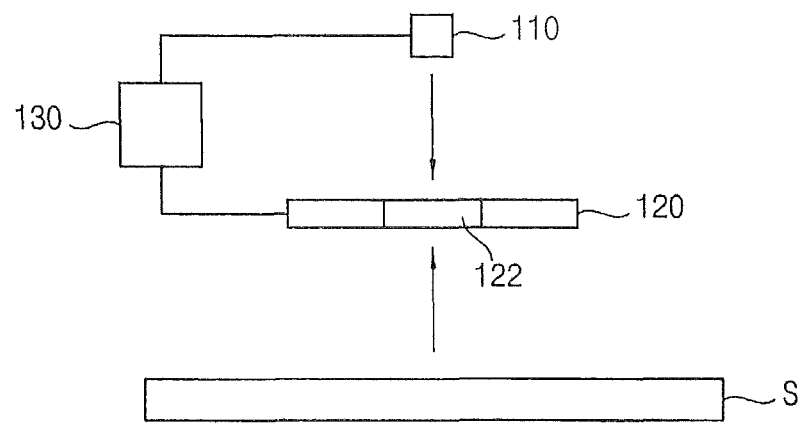

Various example embodiments will be described more fully hereinafter with reference to the accompanying drawings, in which some example embodiments are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

Apparatus for Detecting a Defect of a Substrate

Figure 2:
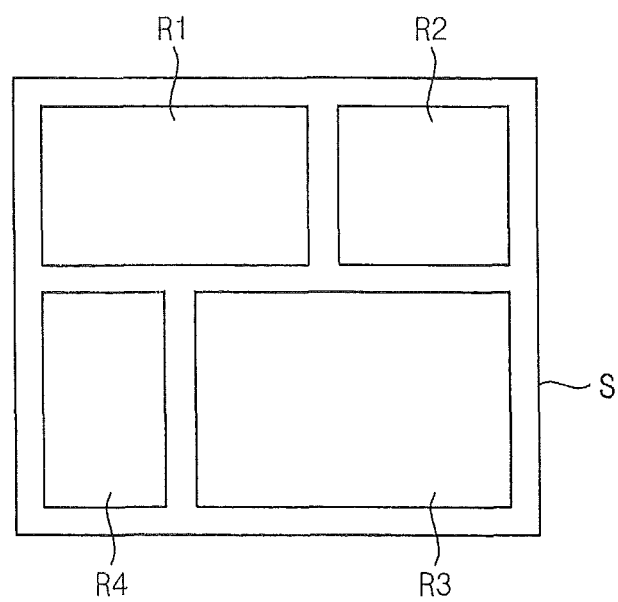
Figure 3:
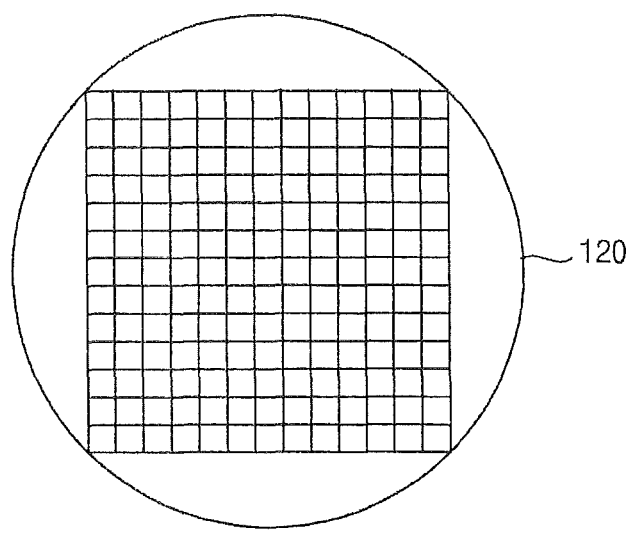
Figure 4:
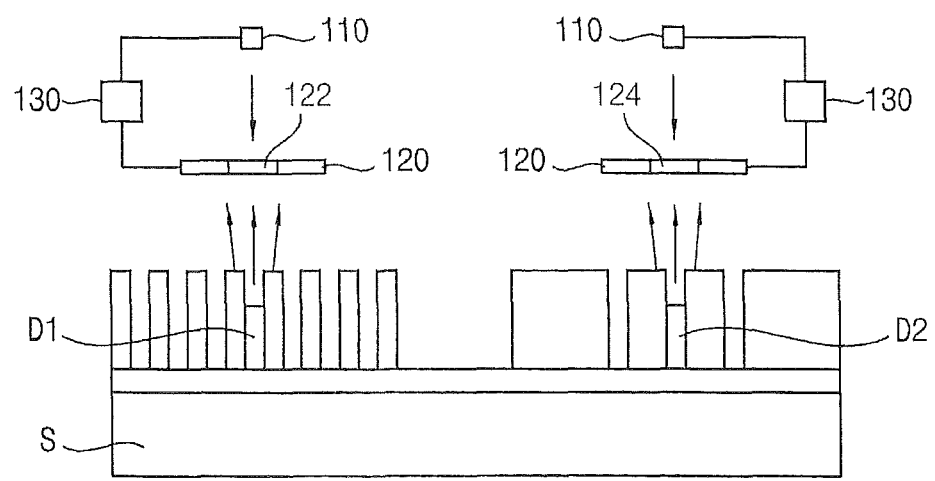

FIG. 1 is a cross-sectional view illustrating an apparatus for detecting a defect of a substrate in accordance with example embodiments, FIG. 2 is a plan view illustrating regions of the substrate, FIG. 3 is a plan view illustrating a spatial light modulator of the apparatus in FIG. 1, FIG. 4 is a cross-sectional view illustrating operations of the apparatus in FIG. 1, and FIGS. 5 to 8 are pictures showing different apertures of the spatial light modulator by the regions of the substrate in FIG. 3.

Referring to FIG. 1, an apparatus 100 for detecting a defect of a substrate in accordance with this example embodiment may include an irradiator 110, a spatial light modulator 120 and a controller 130.

The irradiator 110 may be arranged over the substrate S. The irradiator 10 may irradiate a light to the substrate S. In example embodiments, the substrate S may be or include a semiconductor substrate. Referring to FIG. 2, the semiconductor substrate S may have a plurality of regions. In example embodiments, the semiconductor substrate S may have a first region R1, a second region R2, a third region R3 and a fourth region R4. For example, the first region R1 may include a cell region. The second region R2 may include a peripheral region.

Referring again to FIG. 1, the spatial light modulator 120 may be positioned between the irradiator 110 and the semiconductor substrate S. The spatial light modulator 120 may have an aperture 122 through which the light irradiated from the irradiator 110 may pass. Referring to FIG. 3, a size and/or shape of the aperture 122 in the spatial light modulator 120 may be changed by an electrical or optical technique. For example, a liquid crystal technique or a micro-electro-mechanical system (MEMS) technique may be applied to the spatial light modulator 120. Thus, the size of the aperture 122 may be changed in real time in accordance with the first region R1, the second region R2, the third region R3 and the fourth region R4 of the semiconductor substrate S by electrically or optically controlling the spatial light modulator 120.

Referring again to FIG. 1, the controller 130 may analyze reflected lights from the first region R1, the second region R2, the third region R3 and the fourth region R4 of the semiconductor substrate S to detect defects in the first region R1, the second region R2, the third region R3 and the fourth region R4. In example embodiments, the controller 130 may control the irradiator 110 and the spatial light modulator 120. Further, inspect or inspection recipes such as intensities of the lights and the sizes of the aperture 122 for the first region R1, the second region R2, the third region R3 and the fourth region R4 of the semiconductor substrate S may be set in or by the controller 130. Furthermore, defect detection recipes for the first region R1, the second region R2, the third region R3 and the fourth region R4 of the semiconductor substrate S may be set in or by the controller 130. Particularly, data accumulated by numerous inspections of the semiconductor substrates S may be stored in a database. The inspect recipes and the defect detection recipes for the first region R1, the second region R2, the third region R3 and the fourth region R4 of the semiconductor substrate S may be obtained from the database. The inspect recipes and the defect detection recipes may also be input into the controller 130.

In example embodiments, the controller 130 may selectively change the intensities of the lights irradiated from the irradiator 110 in accordance with the first region R1, the second region R2, the third region R3 and the fourth region R4 of the semiconductor substrate S. For example, the controller 130 may control the irradiator 110 to irradiate a first light having a first intensity to the first region R1 of the semiconductor substrate S. The controller 130 may control the irradiator 110 to irradiate a second light having a second intensity to the second region R2 of the semiconductor substrate S. The controller 130 may control the irradiator 110 to irradiate a third light having a third intensity to the third region R3 of the semiconductor substrate S. The controller 130 may control the irradiator 110 to irradiate a fourth light having a fourth intensity to the fourth region R4 of the semiconductor substrate S. Further, the controller 130 may provide the lights with the intensities set for a particular region at a time when any one of the first region R1, the second region R2, the third region R3 and the fourth region R4 is to be inspected (e.g., after inspection of another region). The regions R1, R2, R3, R4 may be inspected sequentially.

In example embodiments, the controller 130 may selectively change the aperture of the spatial light modulator 120 by the first region R1, the second region R2, the third region R3 and the fourth region R4 of the semiconductor substrate S. For example, the controller 130 may electrically or optically control the spatial light modulator 120 to form a first aperture 122 in FIG. 5, a second aperture 124 in FIG. 6, a third aperture 126 in FIG. 7 and a fourth aperture 128 in FIG. 8 in accordance with the first region R1, the second region R2, the third region R3 and the fourth region R4 of the semiconductor substrate S. The first aperture 122, the second aperture 124, the third aperture 126 and the fourth aperture 128 may vary in accordance with sizes, arrangements, etc., of patterns in the first region R1, the second region R2, the third region R3 and the fourth region R4 of the semiconductor substrate S. Further, the controller 130 may provide the aperture with the sizes set by each of the regions at the time when any one of the first region R1, the second region R2, the third region R3 and the fourth region R4 is to be inspected (e.g., after inspection of another one of the regions R1, R2, R3, R4).

For example, a first defect D1 in the first region R1 of the semiconductor substrate S as the cell region may be accurately detected using the first light having the first intensity and the first aperture 122. A second defect D2 in the second region R2 of the semiconductor substrate S as the peripheral region may be accurately detected using the second light having the second intensity and the second aperture 124. The intensities of the lights and the sizes of the aperture may be obtained from the above-mentioned numerous previous inspections.

Figure 5:
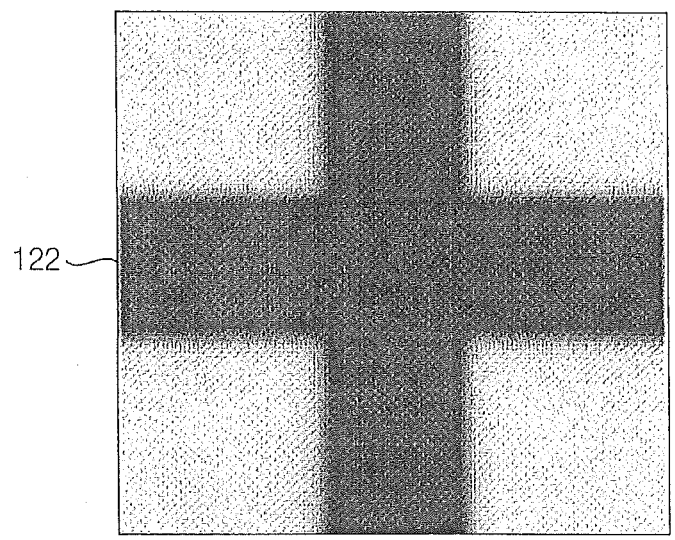

In example embodiments, when the first region R1 of the semiconductor substrate S is to be inspected, the controller 130 may electrically or optically control the spatial light modulator 120 to form the first aperture 122 in FIG. 5. The first light having the first intensity may be irradiated to the first region R1 of the semiconductor substrate S through the first aperture 122. The controller 130 may analyze a first reflected light from the first region R1 to detect a defect in the first region R1 based on a first defect detection recipe.

Figure 6:
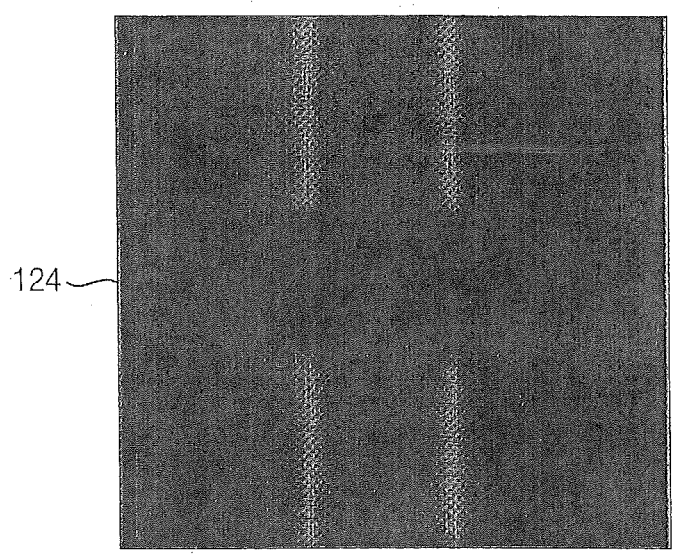

When the second region R2 of the semiconductor substrate S is to be inspected, the controller 130 may electrically or optically control the spatial light modulator 120 to form the second aperture 124 in FIG. 6. The second light having the second intensity may be irradiated to the second region R2 of the semiconductor substrate S through the second aperture 124. The controller 130 may analyze a second reflected light from the second region R2 to detect a defect in the second region R2 based on a second defect detection recipe.

Figure 7:
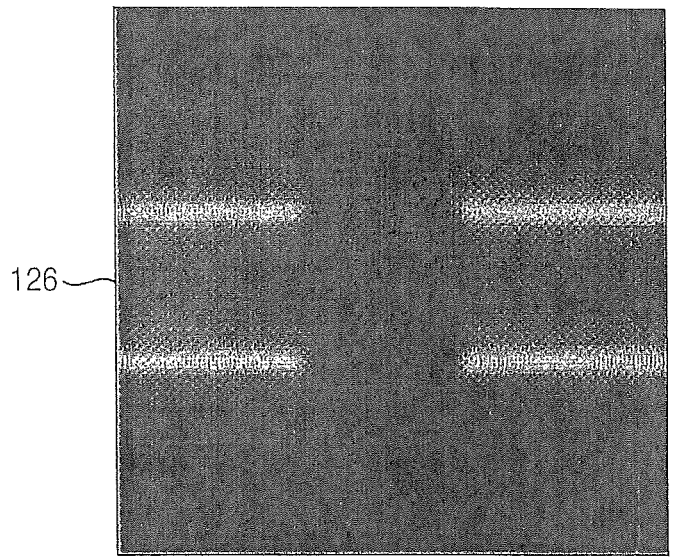

When the third region R3 of the semiconductor substrate S is to be inspected, the controller 130 may electrically or optically control the spatial light modulator 120 to form the third aperture 126 in FIG. 7. The third light having the third intensity may be irradiated to the third region R3 of the semiconductor substrate S through the third aperture 126. The controller 130 may analyze a third reflected light from the third region R3 to detect a defect in the third region R3 based on a third defect detection recipe.

Figure 8:
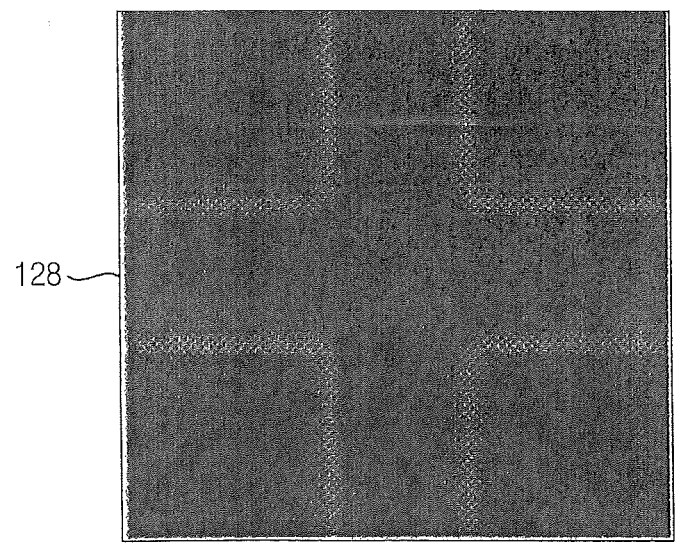

When the fourth region R4 of the semiconductor substrate S is to be inspected, the controller 130 may electrically or optically control the spatial light modulator 120 to form the fourth aperture 128 in FIG. 8. The fourth light having the fourth intensity may be irradiated to the fourth region R4 of the semiconductor substrate S through the fourth aperture 128. The controller 130 may analyze a fourth reflected light from the fourth region R4 to detect a defect in the fourth region R4 based on a fourth defect detection recipe.

In example embodiments, the intensity of the light may be determined in accordance with the size of the aperture. For example, when the aperture has a small size, the light may have a low intensity. In contrast, when the aperture has a large size, the light may have a high intensity. Alternatively, the intensity of the light may be determined regardless of the size of the aperture.

According to this example embodiment, when the region of the semiconductor substrate to be inspected is changed to another region, the controller may change in real time the intensity of the light and the size of the aperture corresponding to the appropriate region of the semiconductor substrate. Therefore, the defects in all of the regions of the semiconductor substrate may be accurately detected in a short time by only one scanning the semiconductor substrate.

Method of Detecting a Defect of a Substrate

Figure 9A:
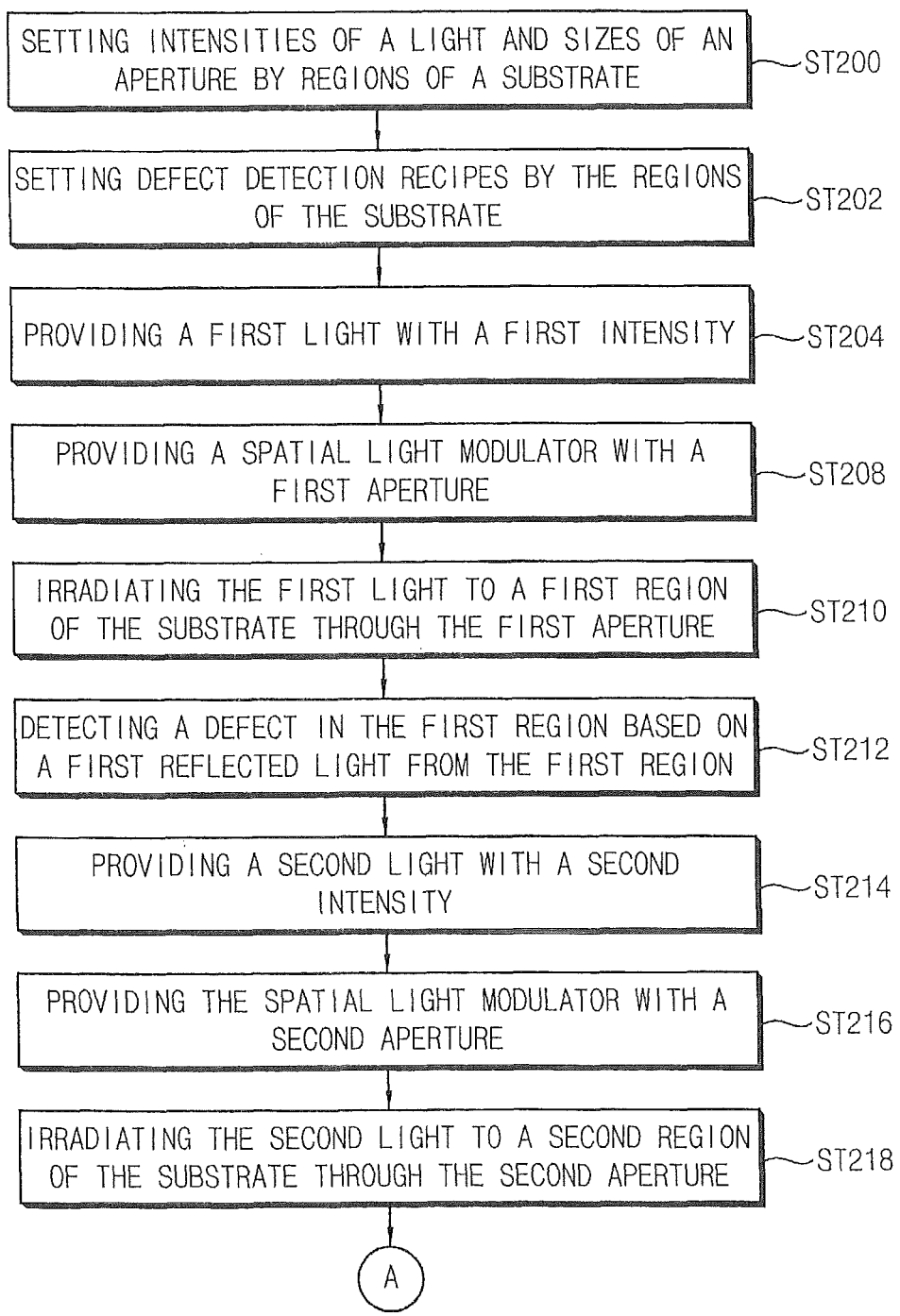
FIGS. 9A and 9B are flow charts illustrating a method of detecting a defect of a substrate using the apparatus in FIG. 1.
Figure 9B:
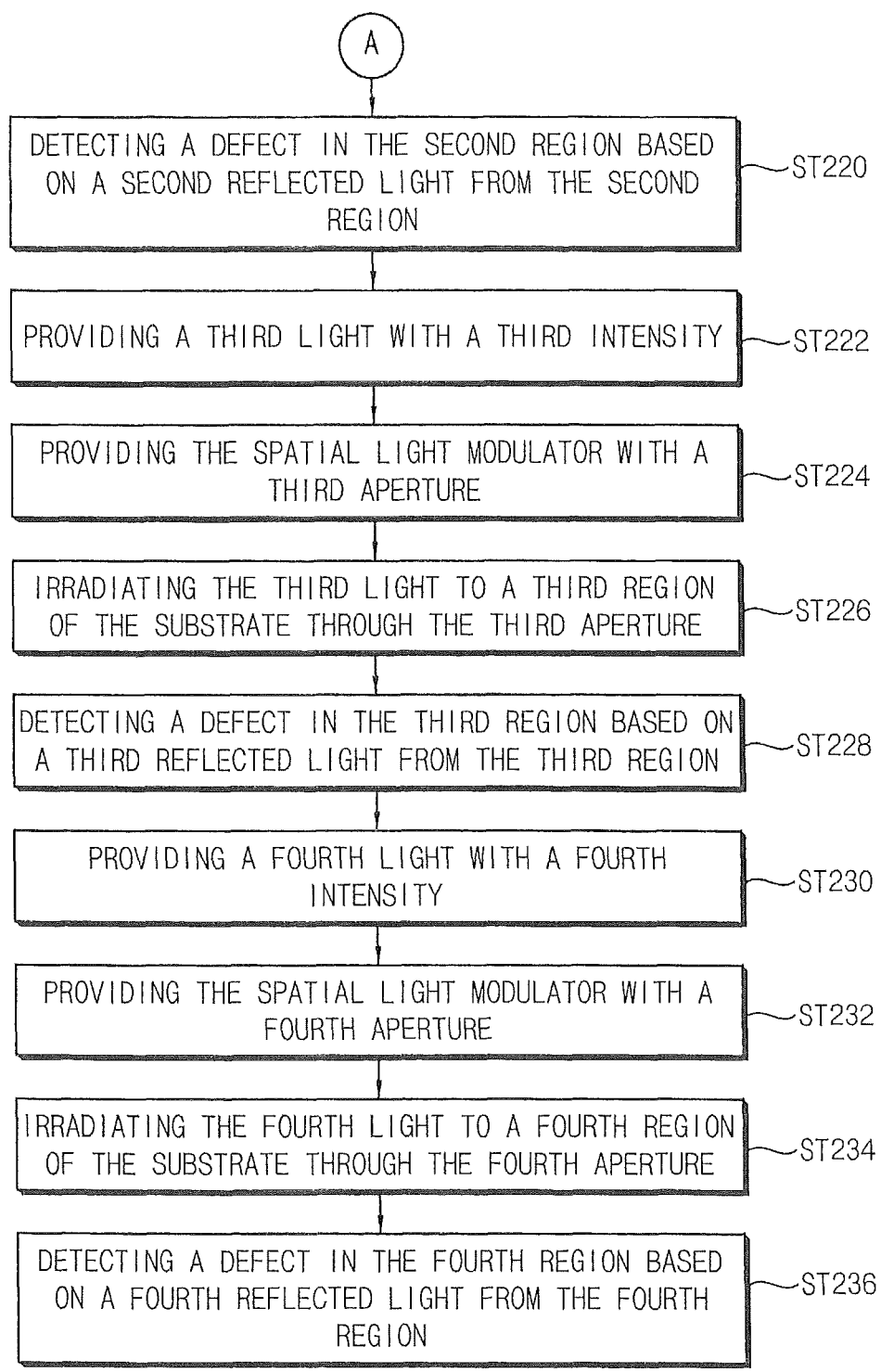

FIGS. 9A and 9B are flow charts illustrating a method of detecting a defect of a substrate using the apparatus in FIG. 1.

Referring to FIGS. 1, 9A and 9B, in step ST200, the intensities of the lights and the sizes of the aperture by the first region R1, the second region R2, the third region R3 and the fourth region R4 of the semiconductor substrate S may be set in the controller 130. In example embodiments, the first intensity of the first light and the first aperture 122 with respect to the first region R1 may be set in the controller 130. The second intensity of the second light and the second aperture 124 with respect to the second region R2 may be set in the controller 130. The third intensity of the third light and the third aperture 126 with respect to the third region R3 may be set in the controller 130. The fourth intensity of the fourth light and the fourth aperture 128 with respect to the fourth region R4 may be set in the controller 130.

In step ST202, the defect detection recipes by the first region R1, the second region R2, the third region R3 and the fourth region R4 of the semiconductor substrate S may be set in the controller 130. In example embodiments, the first defect detection recipe with respect to the first region R1 may be set in the controller 130. The second defect detection recipe with respect to the second region R2 may be set in the controller 130. The third defect detection recipe with respect to the third region R3 may be set in the controller 130. The fourth defect detection recipe with respect to the fourth region R4 may be set in the controller 130.

In step ST204, when the first region R1 of the semiconductor substrate S is to be inspected, the controller 130 may control the irradiator 110 to provide the first light with the first intensity. Thus, the irradiator 110 may emit the first light having the first intensity.

In step ST208, the controller 130 may control the spatial light modulator 120 to form the first aperture 122. In example embodiments, the controller 130 may electrically or optically control the spatial light modulator 120 to form the first aperture 122 in the spatial light modulator 120 through which the first light may pass.

In step ST210, the first light having the first intensity may be irradiated to the first region R1 through the first aperture 122. In example embodiments, the first light having the first intensity and the first aperture 122 may be optimized to the inspection recipe of the first region R1 so that the defect in the first region R1 may be accurately detected using the first light having the first intensity and the first aperture 122.

In step ST212, the controller 130 may analyze the first reflected light from the first region R1 to detect the defect in the first region R1.

In step ST214, when the inspection region may be changed from the first region R1 to the second region R2, the controller 130 may control the irradiator 110 to provide the second light with the second intensity. Thus, the irradiator 110 may emit the second light having the second intensity.

In step ST216, the controller 130 may control the spatial light modulator 120 to form the second aperture 124. In example embodiments, the controller 130 may electrically or optically control the spatial light modulator 120 to form the second aperture 124 in the spatial light modulator 120 through which the second light may pass.

In step ST218, the second light having the second intensity may be irradiated to the second region R2 through the second aperture 124. In example embodiments, the second light having the second intensity and the second aperture 124 may be optimized to the inspection recipe of the second region R2 so that the defect in the second region R2 may be accurately detected using the second light having the second intensity and the second aperture 124.

In step ST220, the controller 130 may analyze the second reflected light from the second region R2 to detect the defect in the second region R2.

In step ST222, when the inspection region may be changed from the second region R2 to the third region R3, the controller 130 may control the irradiator 110 to provide the third light with the third intensity. Thus, the irradiator 110 may emit the third light having the third intensity.

In step ST224, the controller 130 may control the spatial light modulator 120 to form the third aperture 126. In example embodiments, the controller 130 may electrically or optically control the spatial light modulator 120 to form the third aperture 126 in the spatial light modulator 120 through which the third light may pass.

In step ST226, the third light having the third intensity may be irradiated to the third region R3 through the third aperture 126. In example embodiments, the third light having the third intensity and the third aperture 126 may be optimized to the inspection recipe of the third region R3 so that the defect in the third region R3 may be accurately detected using the third light having the third intensity and the third aperture 126.

In step ST228, the controller 130 may analyze the third reflected light from the third region R3 to detect the defect in the third region R3.

In step ST230, when the inspection region may be changed from the third region R3 to the fourth region R4, the controller 130 may control the irradiator 110 to provide the fourth light with the fourth intensity. Thus, the irradiator 110 may emit the fourth light having the fourth intensity.

In step ST232, the controller 130 may control the spatial light modulator 120 to form the fourth aperture 128. In example embodiments, the controller 130 may electrically or optically control the spatial light modulator 120 to form the fourth aperture 128 in the spatial light modulator 120 through which the fourth light may pass.

In step ST234, the fourth light having the fourth intensity may be irradiated to the fourth region R4 through the fourth aperture 128. In example embodiments, the fourth light having the fourth intensity and the fourth aperture 128 may be optimized to the inspection recipe of the fourth region R4 so that the defect in the fourth region R4 may be accurately detected using the fourth light having the fourth intensity and the fourth aperture 128.

In step ST236, the controller 130 may analyze the fourth reflected light from the fourth region R4 to detect the defect in the fourth region R4.

In example embodiments, the semiconductor substrate may include the four regions. Alternatively, the semiconductor substrate may have two regions, three regions or at least five regions. Further, the substrate may include other substrates such as a glass substrate.

According to example embodiments, the spatial light modulator may be controlled in real time in accordance with the regions of the substrate to change the size of the aperture and the intensity of the light so that the defects in the regions of the substrate may be accurately detected. Further, the defect may be detected by scanning the substrate only once so that a time for detecting the defect may be remarkably reduced.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present invention. Accordingly, all such modifications are intended to be included within the scope of the present invention as defined in the claims.

What is claimed is:

1. A method of detecting a defect of a substrate, the method comprising:

irradiating a first light having a first intensity to a first region of the substrate through a first aperture to provide a first reflected light;

detecting a defect in the first region based on the first reflected light from the first region;

changing the first light into a second light having a second intensity at a time when an inspection region is changed from the first region to a second region of the substrate, wherein the second region is different than the first region;

changing the first aperture into a second aperture at the time when the inspection region is changed from the first region to the second region, wherein changing the first aperture into the second aperture comprises controlling a spatial light modulator, and wherein the first and second apertures are defined in the spatial light modulator;

irradiating the second light to the second region of the substrate through the second aperture to provide a second reflected light; and detecting a defect in the second region based on the second reflected light from the second region.

2. An apparatus for detecting a defect of a substrate, the apparatus comprising:

an irradiator configured to irradiate a light to the substrate;

a spatial light modulator arranged between the substrate and the irradiator, the spatial light modulator having an aperture through which the light passes; and a controller configured to control the irradiator to provide the light with different intensities for different regions of the substrate, to control the spatial light modulator to change a size of the aperture for different regions of the substrate, and to detect the defect in the substrate based on a reflected light from the substrate.

3. The apparatus of claim 2, wherein the controller is configured to change the intensities of the light at a time when an inspection region is changed from any one region of the substrate to another region of the substrate.

4. The apparatus of claim 3, wherein the controller is configured to change the size of the aperture at the time when an inspection region is changed.

5. The apparatus of claim 2, wherein the controller is configured to change the size of the aperture at a time when an inspection region is changed from any one region of the substrate to another region of the substrate.

6. The apparatus of claim 2, wherein the controller is configured to store the intensity of the light and the size of the aperture for each of the regions of the substrate.

7. The apparatus of claim 2, wherein the controller is configured to store a defect detection recipe for each of the regions of the substrate.

* * * * *